(12) United States Patent
Spycher et al.

(10) Patent No.: US 7,315,632 B2
(45) Date of Patent: Jan. 1, 2008

(54) DEVICE FOR IMAGING THE PAPILLARY LINES OF A FINGER

(75) Inventors: Martin Spycher, Zurich (CH); Anne-Sophie Golsong Roosdorp, Zug (CH)

(73) Assignee: Fingerpin AG, Zurich (CH)

( * ) Notice: Subject to any disclaimer, the term of this patent is extended or adjusted under 35 U.S.C. 154(b) by 654 days.

(21) Appl. No.: 10/451,406

(22) PCT Filed: Nov. 29, 2001

(86) PCT No.: PCT/CH01/00689

§ 371 (c)(1),
(2), (4) Date: Jan. 22, 2004

(87) PCT Pub. No.: WO02/052491

PCT Pub. Date: Jul. 4, 2002

(65) Prior Publication Data

US 2004/0114783 A1 Jun. 17, 2004

(30) Foreign Application Priority Data

Dec. 22, 2000 (EP) ................................. 00811232

(51) Int. Cl.
*G06K 9/00* (2006.01)
(52) U.S. Cl. ................. 382/124; 382/127; 250/227.28; 356/71

(58) Field of Classification Search ........ 382/124–125, 382/127, 126, 116; 356/71, 39, 398; 250/227.28, 250/227.11; 600/473, 475, 476
See application file for complete search history.

(56) References Cited

U.S. PATENT DOCUMENTS

| | | | |
|---|---|---|---|
| 4,681,435 A | | 7/1987 | Kubota et al. |
| 5,096,290 A | * | 3/1992 | Ohta ........................... 356/71 |
| 5,233,404 A | | 8/1993 | Lougheed et al. |
| 5,621,516 A | * | 4/1997 | Shinzaki et al. .............. 356/71 |
| 5,623,553 A | | 4/1997 | Sekiya |
| 5,796,858 A | * | 8/1998 | Zhou et al. .................. 382/127 |
| 6,115,483 A | * | 9/2000 | Suga ........................... 382/127 |
| 6,127,674 A | | 10/2000 | Shinzaki et al. |
| 6,175,407 B1 | * | 1/2001 | Sartor ........................ 356/71 |

FOREIGN PATENT DOCUMENTS

| WO | WO 01/18741 | 3/2001 |
|---|---|---|
| WO | WO 01/88835 | 11/2001 |

* cited by examiner

*Primary Examiner*—Sheela Chawan
(74) *Attorney, Agent, or Firm*—Browdy and Neimark, PLLC

(57) ABSTRACT

Device has a transparent body (1) with a support surface (2). Light is incident on the surface at an angle less than that required for total internal reflection. In the areas of the fingerprint ridges evanescent fields are excited. Propagated light (12-14) is reflected from the surface (2) and incident on a detector (22) at angles within the angular range for total internal reflection.

15 Claims, 4 Drawing Sheets

DEVICE FOR IMAGING THE PAPILLARY LINES OF A FINGER

TECHNICAL FIELD

The invention relates to an apparatus for optically recording and compiling a contrast image of the papillary ridges on the surface of a finger. It is used, for example, in a system for access control for the purpose of identifying or verifying persons. In the case of the optical recording of the papillary ridges, it is, in particular, the total internal reflection of light beams at the surface of the finger which is laid onto a transparent body that is applied.

PRIOR ART

Such units for optically recording a contrast image of the papillary ridges of a finger have a prism or a similar transparent body on whose surface the finger is laid. The papillary ridges, which are to be imaged, of the finger are illuminated by a light source that is arranged below the prism and passes its light onto the papillary ridges through the transparent body. It is known that when light falls at angles of incidence greater than or equal to a critical angle onto an interface between a denser medium such as, for example, glass and a less dense medium such as, for example, air, [lacuna] experiences total internal reflection and is retroreflected into the denser medium. The critical angle is $\vartheta_{crit}=\sin^{-1}(n_2/n_1)$, $n_2$ being the optical refractive index of the less dense medium, and $n_1$ being the optical refractive index of the denser medium, and $\vartheta_{crit}$ being the angle between the normal to the interface and the incident as well as also the totally reflected light beam. If, however, an object is located at the interface or in the immediate vicinity of the interface, light can emerge from the prism, something which is known as prevented total internal reflection. This phenomenon is applied for optically recording the papillary ridges of a finger by means of total internal reflection. A typical arrangement is disclosed, for example, in Optics & Photonics News, October 2000, pages 24-25. There, a light source is directed onto one of the 45° faces of a prism such that its light falls through the prism from below onto the hypotenuse of the prism, the angle of incidence onto the hypotenuse being greater than the critical angle for total internal reflection. A finger lies on the surface of the hypotenuse, but the finger is not in uniform contact with the prism. Specifically, of the papillary ridges on the finger skin, only the peaks of the ridges are in contact with the prism, and the troughs of the ridges are moved a small distance from the prism surface. In those regions where the peaks of the ridges are located, the light experiences prevented total internal reflection and emerges from the prism. In the troughs, where air is located in a region greater than the so-called evanescent decay distance (which is typically approximately 1 micrometer), the light is totally reflected and passes through the prism and an imaging optical system to an imaging surface. A contrast image of the papillary ridges of the finger is produced there in which the peaks appear bright and the troughs dark.

Such an arrangement for recording the papillary ridges of a finger permits a contrasting image of the papillary ridges if the finger is dry and air is located in the troughs of the ridges. However, if the finger is wet or oily, which frequently occurs in practice on warm days, for example, the condition for total internal reflection is changed since it is now water or oil instead of air that is located on the prismatic surface and, in particular, in the troughs of the ridges. The critical angle for total internal reflection is then greater because of the higher refractive index of water or oil than in the case of air on the prismatic surface. In this case, the light also experiences prevented total internal reflection in the regions of the troughs and exits from the prism and into the water or oil. It is thus no longer reflected. The contrast of the image is thereby largely lost. Furthermore, the imaging is further falsified by light that scatters on the main surfaces after penetration of the water or oil and passes back into the prism.

SUMMARY OF THE INVENTION

The present invention is based on the object of creating an apparatus for recording an optical contrast image of a papillary ridge pattern of a finger, in the case of which apparatus the light experiences total internal reflection on the support surface for the finger. In particular, the above-mentioned disadvantages of the prior art are to be avoided, and a high contrast of the image of the papillary ridge pattern is to be achieved independently of the properties of the finger surface such as, for example, wet or dry.

This object is achieved by means of an apparatus in accordance with claim 1.

The apparatus has a transparent body with a boundary surface that serves as support surface for the finger surface to be imaged. A light source is arranged such that its light radiates through the transparent body and falls onto the boundary surface of the body on which the finger lies. Furthermore, the apparatus has a light detector and an imaging optical system whose optical axis leads through a lateral surface of the transparent body. According to the invention, the angle of incidence of the light from the light source onto the interface is smaller than the critical angle for total internal reflection at the interface of the transparent body with air lying thereabove. The imaging optical system is designed such that it captures and directs onto the light detector only light beams that emanate from the support surface of the transparent body at an angle to the normal to the support surface that is equal to or greater than the critical angle for total internal reflection at the interface between the transparent body with water, oil or similar medium lying thereon.

The light that falls from the light source onto the interface through the transparent body passes for the most part through the interface and to the finger lying thereupon, since the angle of incidence of the light is smaller than or equal to the critical angle for total internal reflection at the interface. (Only a small portion, approximately 4%, of the light emitted by the light source is spectrally reflected.) The light is scattered on the surface of the papillary ridges or in the interior of the finger. The light scattered in the interior of the finger is partially totally internally reflected at the interface between the finger and air, water or oil, and generates at the finger surface an evanescent field that decays exponentially in the space outside the finger surface. The evanescent decay distance or 1/e depth is the distance from the finger surface for which the field strength of the electromagnetic field is still 1/e of the field strength of the electromagnetic field at the finger surface. The surfaces of the troughs of the papillary ridges are located near the support surface, and the distance between their surfaces and the support surface is smaller than the evanescent distance, or lies in the region of the evanescent decay distance. The evanescent fields emanating from the peaks of the papillary ridges generate propagating waves that radiate into the transparent body.

The entrance angle of the propagating waves generated by evanescent fields in the support surface is equal to the critical or greater than the critical angle for total internal reflection.

The evanescent fields emanating from the troughs of the papillary ridges are too far removed from the support surface to be able to generate waves propagating in the transparent body with a field strength that is still significant. Since the field strength decreases exponentially with the distance of the corresponding finger part from the support surface, the result is a high contrast between the peaks and the troughs of the papillary ridges.

The imaging optical system is arranged such that it only directs light from the support surface or its object surface onto the light detector that propagates within the angular range for total internal reflection. Light beams that are produced by the excitation of evanescent fields between the peaks of the ridges and the interface propagate in this range. The evanescent light waves emanating from the regions of the troughs of the papillary ridges are unable to generate any propagating light waves of acceptable field strength in this angular range. Thus, no light that propagates in this angular range and could be detected by the light detector emerges from the troughs. The result is a contrast image in which the peaks of the papillary ridges appear bright and the troughs appear dark.

The invention provides the advantage that the quality of the contrast image is maintained irrespective of whether the finger is dry, wet, greasy or oily. Specifically, if the finger is, for example, wet, water is located in the troughs. The light that passes from the light source into the troughs of the papillary ridges filled with water is not scattered there. As in the case of air in the troughs, it propagates through the water to the surfaces of the troughs. Since the latter are relatively far removed from the interface, evanescent fields emanating from there can, in turn, not effect any propagating light waves in the angular region for total reflection. Thus, in the case of a wet finger as well, no light exists from the troughs in the angular range in which the imaging takes place. Evanescent fields are excited in the space between ridge peaks and the interface irrespective of whether the finger surface is wet or dry.

The critical angle for total internal reflection varies depending on the medium of the transparent body and of the medium lying thereon. The critical angle $\vartheta_{crit}$ in the case of water on the finger and at the interface in the regions of the troughs is greater than in the case of air above the interface. In order to detect the propagating light within the angular range for total internal reflection for both cases respectively, the imaging optical system and the light detector are designed such that they detect light from the angular range for total internal reflection in the case of water. With this design, the propagating light waves are detected both in the case of water and in the case of air at the interface, since the critical angle in the case of air is smaller than the critical angle in the case of water. In the case of water, the angular range for total internal reflection coincides in large part with the angular range for total internal reflection in the case of air. The critical angle in the case of water is 62°, and in the case of air 42°, the angular range for total internal reflection, measured from the normal to the interface, ranging from 62° to 90° or from 42° to 90°.

It emerges in practice that the contrast in the image of a wet finger scarcely differs from the contrast of the image of a dry finger. Although the angular range for total internal reflection are of different size for the two applications mentioned, other factors, such as a 1/e depth of different magnitude, for example, contribute to achievement of a comparable contrast in the images.

In a first embodiment of the invention, the light source has a lens or a plurality of lenses for collimation or quasi-collimation of the light sent onto the interface. Consequently, it is clear that no light passes from the light source directly into the angular range for total internal reflection into the imaging optical system and onto the light detector.

In a particular design of the invention, the light source has a plurality of light-emitting diodes that are arranged in a one- or two-dimensional array. The arrangement in an array effects a homogeneous illumination of the boundary surface of the transparent body whereas the light emitted on a surface by a single light-emitting diode frequently exhibits dark rings, the arrangement of a plurality of light-emitting diodes in an array achieves a homogeneous intensity distribution by virtue of the fact that the dark rings of the individual light-emitting diodes are illuminated by neighboring light-emitting diodes in the array. Furthermore, thanks to the lenses integrated in the light-emitting diodes, the emitted light is quasi-collimated or virtually collimated.

In a preferred design of the light source, the light-emitting diodes are arranged such that the intensity distribution is homogeneous in the plane of the light detector. Since the intensity of the light that falls onto the detector is inversely proportional to the square of the path covered by the light, the light-emitting diodes are arranged between the light source and the detector in accordance with the different length of the light path. In a first variant, the light-emitting diodes are arranged in two rows, the emitted intensity of one row corresponding to 70-80% of the emitted intensity of the second row.

In a second variant, the light-emitting diodes are arranged in three rows, the emitted intensity of the middle row being approximately 30-70%, in particular approximately 50%, of the emitted intensity of the first and third rows.

In a further design of the invention, the light-emitting diodes emit in the red wavelength region from 650 nm to 780 nm. In a further design, the light-emitting diodes emit in the infrared wavelength region from 780 nm to 980 nm. The use of infrared light-emitting diodes provides the advantage of an advantageous energy balance for the entire apparatus, since the emitted light intensity per current consumption of the light-emitting diodes is greater than that of red light-emitting diodes. Furthermore, the sensitivity of suitable detectors is higher in this wavelength region.

In a further design, a diffuser is arranged between the light source and the transparent body. The use of a diffuser likewise effects a homogeneous intensity distribution of the light on the boundary surface of the transparent body. It further provides the advantage that fewer light-emitting diodes are required for a desired homogeneity of the intensity distribution on the boundary surface.

In a further design, the imaging optical system has a single lens or a lens system for imaging the papillary ridge pattern on to the detector surface. Conventional lenses and also holographic lenses can be used for this purpose.

In a preferred design of the imaging optical system, a single, focusing lens is integrated on a lateral surface of the transparent body.

In a further design, the imaging optical system has a diaphragm for improving the depth of field of the image on the detector surface. In a particular design, this diaphragm is arranged immediately upstream or downstream of the single integrated lens.

In a further design of the invention, the optical axis of the imaging optical system leads perpendicularly onto the lateral surface of the transparent body such that no optical refraction occurs on the lateral surface which could distort the image of the papillary ridge pattern.

In a further particular design of the invention, there is arranged at a lateral surface of the transparent body a mirror that directs the light emanating from the support surface back into the transparent body. In a first variant, the mirror is a flat mirror, and in a second variant a convex, cylindrical mirror that permits the light in the transparent body to divert easily. The cylindrical mirror provides the advantage of imaging onto the detector surface in the case of which the entire detector surface is completely illuminated.

In a further design of the invention, there is arranged outside the transparent body a further deflecting mirror, which directs the light which enters through the single lens integrated on the lateral surface of the body onto a board on which the light-emitting diodes and the detector are arranged. This arrangement then permits the arrangement of all electric components, the light-emitting diodes and the detector on a common printed circuit board.

A further increase in efficiency is possible by virtue of the fact that there are also arranged at the further lateral walls mirrors that, in turn, is directed for a second time onto the finger light that is not directed usefully onto the detector (for example departing below the critical angle but not falling onto the lens). The silvering can be executed in this case incrementally or similarly, in order to change back the light in an optimized fashion.

All these measures for the imaging optical system, specifically the reflecting mirror on the lateral surface and the integrated focusing lens at another lateral surface, as well as the second deflecting mirror and the use of a common board, have the purpose of miniaturizing the imaging optical system and implementing the apparatus such that space is found for the sensor in a suitably small housing.

In a preferred design, the light detector of the apparatus has a two-dimensional CMOS camera. It permits a relatively simple further processing of the data acquired, for example, for image processing for the purpose of identifying or verifying a person within the framework of a system for admission control or control of access to equipment.

In an alternative design of the invention, the light detector of the apparatus has a CCD camera.

In the apparatus according to the invention, the support surface is aligned at an angle of less than 90° to the optical axis of the imaging system. In a preferred design of the invention in which the Scheimpflug principle is applied, the detector surface is likewise aligned at an angle to the optical axis. The application of the Scheimpflug principle reduces distortions of the image. The arrangement according to this principle attempts, however, to reduce the light intensity on the detector surface. In order to diminish this loss of light intensity, in a particular design the transparent body consists of a high-index material. This has the effect that the critical angle for total internal reflection becomes smaller, since the refractive index of the denser medium becomes greater. Given that the lateral surface of the transparent body is perpendicular to the optical axis of the imaging optical system, the angle between the optical axis and the support surface increases to 90°. Consequently, according to the Scheimpflug principle the angle between the detector surface and optical axis is also enlarged. The loss of light intensity is thereby diminished.

In the particular variant of the invention, the transparent body comprises an, in particular high-refractive-index, plastic such as, for example, PMMA (polymethylmethacrylate), PC (polycarbonate) or COC (cyclic olefin copolymer). The proposed optical system for measuring the papillary ridges can advantageously be combined in this case with a pulse measurement or even with a measurement of the oxygen content in the blood of the finger being analyzed (so-called life test). Furthermore, in order to save current, the illumination can be switched off except for one light source when no finger is resting on the detector. This one, for example, diode in combination with an associated detector, which can either be designed as a separate detector or else can comprise the detector for the papillary ridges, then assumes a monitoring function (light barrier). Light is emitted periodically by the light source, and as soon as the detector receives corresponding reflected signals the other light sources, which serve the purpose of illuminating the papillary ridges, are switched in and the entire unit is activated.

DESIGN OF THE INVENTION

Figure 1:
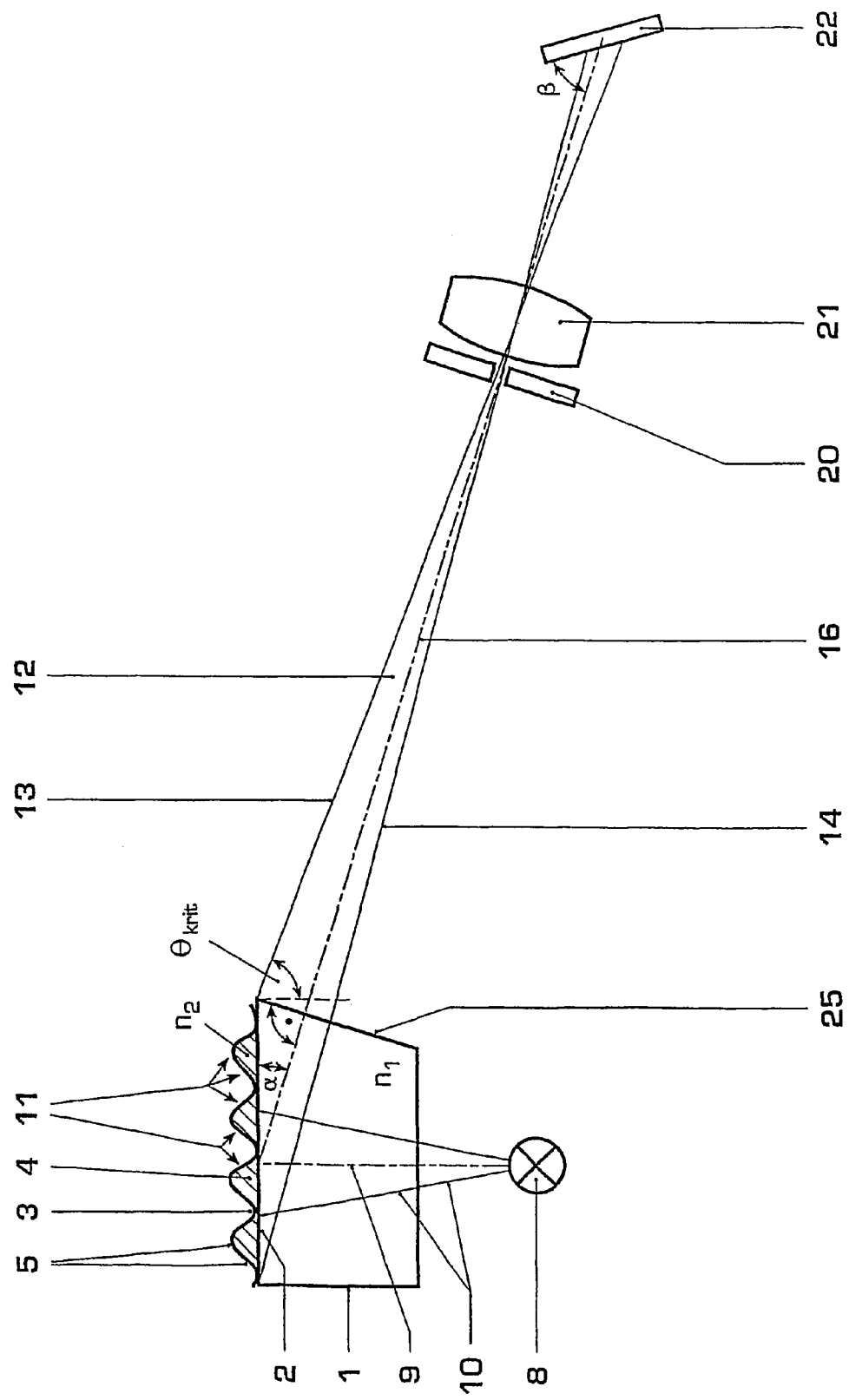
FIG. 1 Shows an illustration of the apparatus for recording the papillary ridges of a finger, with the light source and imaging optical system.

FIG. 1 shows a transparent body 1, for example, made from glass, quartz glass or Plexiglas. Its boundary surface 2 serves as support surface 2 for a finger. Papillary ridges with peaks 3 and troughs 4 are shown here greatly enlarged in contact with the support surface 2. The space between the boundary surface or support surface 2 and the surfaces 5 of the peaks 4 are filled with air, water, oil of the also other clear liquids that can occur on a person's finger. The depth of the troughs is typically 1/10 mm, which is much deeper than a typical 1/e depth.

A light source 8 is arranged below the transparent body 1, the light which exits being directed perpendicularly onto the boundary surface 2. The light source 8 comprises, for example, one or more light-emitting diodes 8 that each have an integrated lens. These lenses for the most part collimate the light which exits, a portion of the light being emitted in an angular range of, for example, 30°. In any case, the angle of incidence of the light on the interface 2 is less than the critical angle for total internal reflection.

Light beams 9 from the light source pass through the transparent body and through the interface 2 onto the surface of the papillary ridges and into the finger, that is to say into the interior of the peaks 3 of the papillary ridges. There, the light is scattered and light beams 10 are produced in all directions.

In the region of the peaks in the immediate vicinity of the interface, that is to say within the 1/e depth, evanescent fields are excited that generate waves 11 propagating in the transparent body 1. These propagate at angles (measured from the normal) that are greater than or equal to the critical angle for total internal reflection. In concrete terms, this critical angle is $\vartheta_{crit}=62°$ for a glass material with a refractive index of $n_1=1.5$ and water on the interface 2 where $n_2=1.33$.

The imaging optical system is designed such that only light beams in the light bundle 12 which emanate from the evanescent fields and propagate in an angular range for total internal reflection are detected. The outer light beams 13 and 14 of the light bundle 12, which are determined by the aperture of the imaging optical system, execute in each case from the edge of the support surface 2 in conjunction with an angle of 65° or 62°. They lead through diaphragm 20 and lens 21 and finally fall onto the light detector 22. The beams in the bundle 12 lie clearly within the angular range for total internal reflection at the interface 2 with water in the troughs 4.

If the finger is dry and there is air instead of water in the troughs 4, the light waves propagate in an angular range of total internal reflection of 42° to 90°. Of these, only the light beams in the angular range from 62° to 90° reach the detector.

The imaging optical system effects imaging of the papillary ridges onto the detector surface of the light detector 22 with a reduction of 4×, the support surface being 18 mm×24 mm (or 11×14 mm and 15×20 mm, respectively, in accordance with other embodiments as described further below in conjunction with FIG. 4 and the following ones), and the detector surface is approximately 4 mm×6 mm (for example CIF or VGA sensors). In the design shown, the imaging optical system comprises a single symmetrical lens with a focal length of 12 mm for 18×24 mm. In a preferred variant, the imaging optical system is folded by means of a planar mirror, as a result of which the apparatus can be in a more compact form. Furthermore, it is also possible to implement folding by means of a curved mirror together with omission of the lens.

The overall system length of the imaging optical system is 80 mm in the example shown. The diaphragm aperture is 1 mm, for example, in order to achieve a sufficient depth of field in the case of an object size of 24 mm as measured on the plane oblique to the optical axis.

The light detector 22 comprises a two-dimensional CMOS camera with an array of 640×480 pixels, for example. Sampling errors or quantification errors can be avoided in this application with the aid of this number of pixels.

The optical axis of the imaging optical system runs perpendicularly through the lateral surface 25 of the transparent body 1. Applying the Scheimpflug principle, the detector surface of the light detector 22 is aligned at an angle α to the optical axis, the object surface or support surface being at an angle β to the optical axis. The angles α and β are 23° and 61°, respectively, in the design shown.

In order to raise the light intensity on the detector surface, the transparent body will consist of a high-index material such as, for example, SF, LaF or LaSF glasses from Schott with a refractive index between 1.65 and 1.9. The use of such high-index glasses effects a reduction in the critical angle $\theta_{crit}$ at 37° or 32°. Since the optical axis of the imaging optical system leads perpendicularly through the lateral surface 25, the angle α between the support surface and the angle β to the detector surface is then also diminished. Since a raised light intensity on the detector surface is achieved by diminishing this angle in this way, less energy is required to illuminate the interface.

Figure 2:
FIG. 2 shows an example of a photograph of the papillary ridges of a dry finger.
Figure 3:
FIG. 3 shows an example of a photograph of the papillary ridges of a wet finger.

FIG. 2 shows a contrast image, compiled by the apparatus according to the invention, of the papillary ridges of a dry finger. The bright region of the contrast image represent the peaks and the dark regions the troughs of the papillary ridges. FIG. 3 shows a contrast image, compiled by the same apparatus, of the same, but wet, finger. The contrast achieved is the same in both images.

Figure 4:
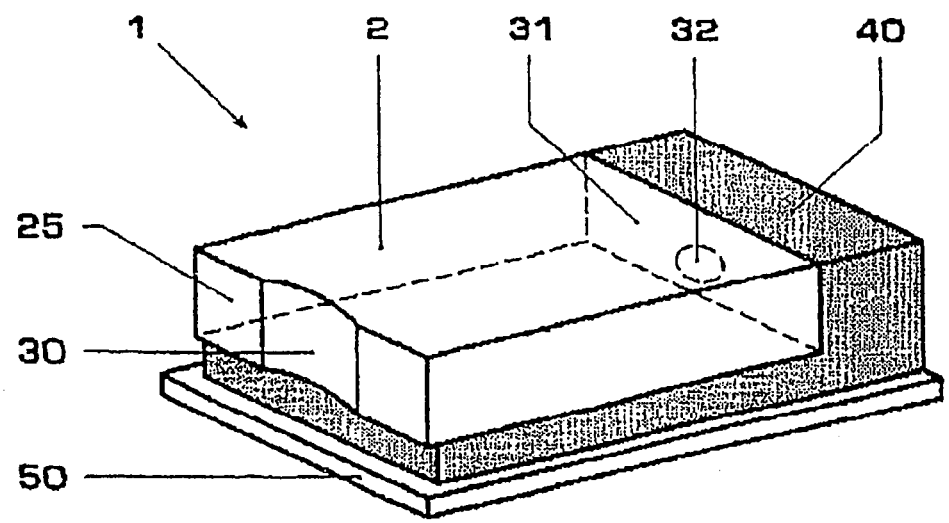
FIG. 4 shows an example of a particular and preferred design of the apparatus according to the invention, with a miniaturized imaging optical system integrated in the transparent body, a mirror holder and a printed circuit board.
Figure 5:
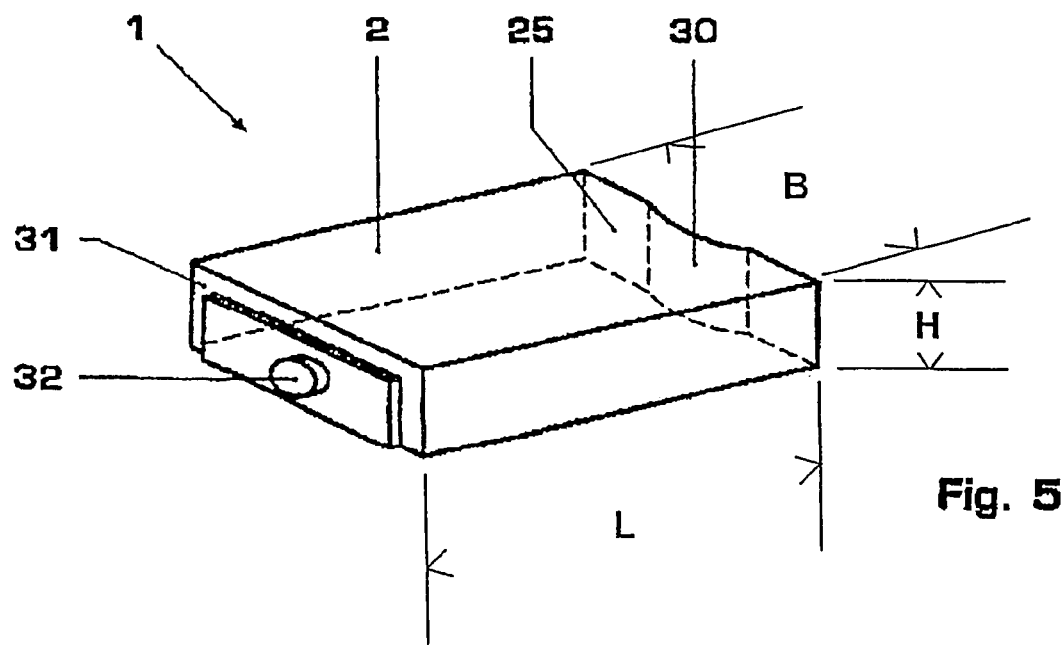
FIG. 5 shows a further view of the transparent body with integrated imaging optical system.

FIG. 4 shows the apparatus according to the invention in a compact implementation with the transparent body 1, a holding block 40 and a printed circuit board 50. A particular feature of this implementation is the integration of a portion of the imaging optical system in the transparent body 1. The transparent body 1 has a support surface 2 on which the finger whose papillary ridges are imaged is laid. In accordance with the apparatus in FIG. 1, the support surface 2 is illuminated from below by a light source that is arranged on the printed circuit board. The beams emanating from the finger fall onto a lateral surface 25 of the transparent body at which a mirror 30 is integrated. The mirror can be mounted in this case, or preferably be vapor-deposited directly onto the material of the transparent body. In accordance with FIG. 4, this mirror 30 is of convex cylindrical design. However, it can also be flat. After reflection at the mirror 30, the beams pass to the other lateral surface 31 of the transparent body at which a focusing lens 32 is integrated. Integrated means that the lens is either directly fitted on the transparent body in a substantially form-fitting fashion, or is fashioned from the block of the transparent body, that is to say the lens and transparent body are designed as a monoblock. The integrated lens is preferably arranged substantially flush with the lower edge of the block 1. The cylindrical mirror has the effect that the rectangular, light-sensitive detector surface of the apparatus is illuminated and used to the full. FIG. 5 shows the same transparent body of FIG. 4 but in a view of the lateral surface 31 with the lens 32 integrated there. The block 1 typically has a length L of 27.5 mm in conjunction with a width B of 22 mm and a height H of 6.1 mm. A larger embodiment has the mass 37.3 mm (L), by 28 mm (B) by 8.2 mm (H). The lateral surface denoted by 25, in which the mirror 30 is integrated, is inclined to the support surface 2 so that the light beams, which are directed from the support surface 2 onto the mirror 30, enter through the integrated lens 32 in a fashion parallel to the support surface 2 on the opposite side, and distortions are thus avoided. With the specified dimensions on the transparent body, in other words the angle between the support surface 2 and lateral surface 25 is not 90 degrees but in the region of 83 degrees. In the case of the larger embodiment, this angle is 82 degrees. The mirror 30, which is integrated in this inclined lateral surface 25, also has a shape that prevents the image of the finger resting on the support surface 2 arriving on the detector from not being distorted as far as possible (that is to say preferably a rectangular image given a rectangular finger support surface). This shape can be, for example, cylindrical, but can also assume a more complex form that is calculated from the paths of the light beams between the support surface 2 and detector.

Figure 6:
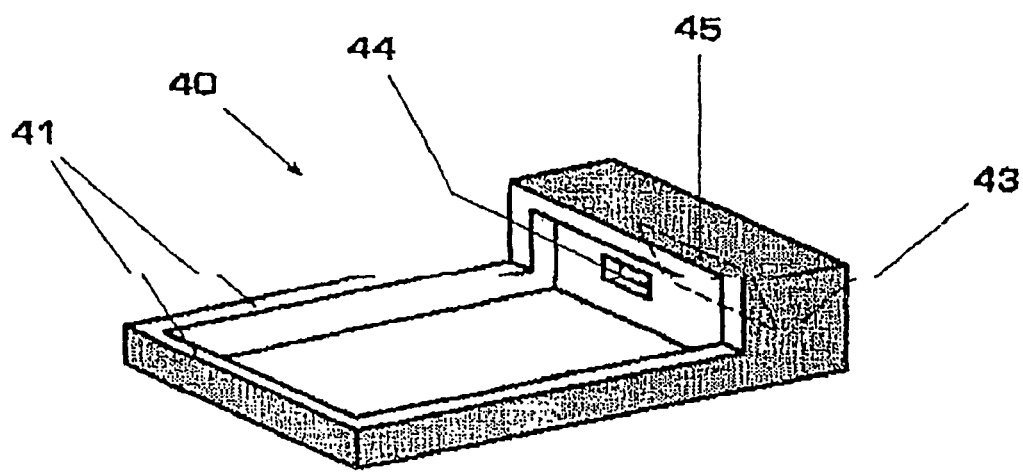
FIG. 6 shows the mirror holder of the apparatus according to the invention.
Figure 7:
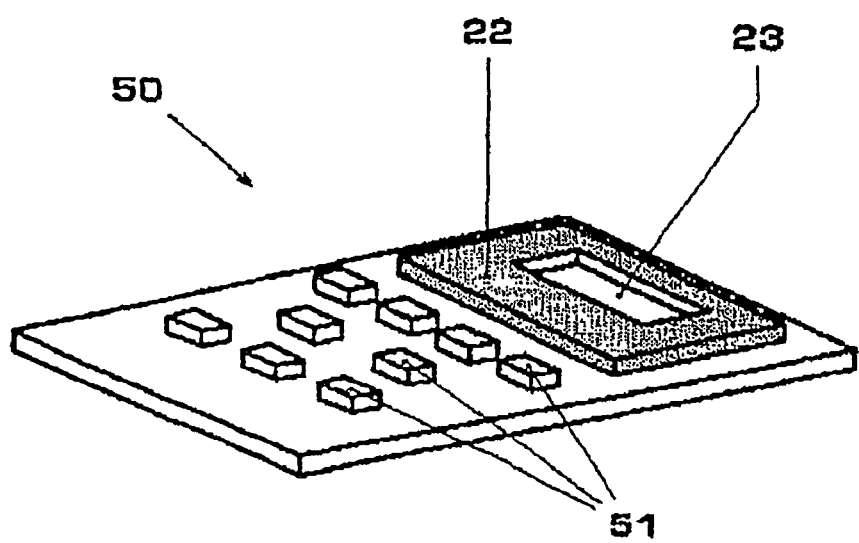
FIG. 7 shows the printed circuit board with an example of the arrangement of the light source.

FIG. 6 shows the holding block 40. It has a frame 41 on which the transparent body comes to lie. A diaphragm 44 and a deflecting mirror 45 are arranged in a side part 43 that bears against the lateral surface 31 of the transparent body. The light that has been focused by the lens 32 and has entered through the diaphragm 44 is directed downward by the deflecting mirror 45 to the printed circuit board 50 in accordance with FIG. 7. A plurality of light-emitting diodes 51 in rows and the light detector 22 with the rectangular light-sensitive detector surface 23 are arranged on the printed circuit board 50. The light-emitting diodes are arranged in three rows in the example shown. It is preferred to effect a homogeneous illumination of the detector surface 23. The light path lengths of different beams which pass from the light source to the support surface of the transparent body and via mirror and lens to the light detector are, however, very different. Where the intensity of all the light-emitting diodes is the same, the intensity distribution on the light detector would be correspondingly inhomogeneous because of the intensity falling off with the square of the light path length. For this reason, the light-emitting diodes are driven at different performance levels in a preferred method for operating the apparatus. The light-emitting diodes of the arrangement shown are driven, for example, such such that the outgoing intensity of the middle row is 50% of the intensity of the two outer rows. In further arrangements, for example with two rows of light-emitting diodes, the outgoing intensity of one row is approximately 80% of the intensity of the other row.

It is also possible in the arrangement of the diodes 51 to fit only the two outer rows, in which 3 and 4 diodes are arranged, respectively, with diodes that serve the purpose of illuminating the papillary ridges. A further light-emitting diode and a separate detector can then be arranged in the middle row. This specific light-emitting diode in the middle row can then take over the function of a light barrier. This is done, specifically, in such a way that it is normally only this diode that is activated and periodically emits light signals. Only once a finger is laid onto the support surface 2 is the light from this diode reflected and received by the separate detector. As soon as this separate detector now receives a signal, the remainder is activated, that is to say the other diodes serving to illuminate the papillary ridges are switched on and the measurement of the papillary ridges is activated. Since the diodes normally consume a great deal of current and a permanent illumination of the support surface 2 should therefore be avoided, the current consumption of the unit can be substantially reduced by illuminating only when a finger really is lying on the support surface 2. In this case, the separate detector need not necessarily be directly irradiated, but it can also be irradiated indirectly with the use of an optical guide that prevents ambient light from disturbing the measurement. This diode arranged in the middle row can, however, also be used additionally for a so-called life test (for example pulse oxymetry). In this case, transmitters and/or receivers for pulse oxymetry can also be arranged laterally on the block. That is to say, they can be used for the purpose, for example, of measuring the pulse and/or the oxygen content in the blood of the laid finger in order to ensure that a living finger and not an artificial simulation is resting on the support surface 2. If the diodes provided for illuminating the support surface are being operated, for example, at a frequency of 650 nm, a further frequency is required for measuring the oxygen content. For this purpose the diode in the middle row can be operated, for example, at a frequency of 850 nm, and the oxygen content can be determined by comparing the two measurements at two different frequencies. The two different frequencies can be measured on the same separate detector.

LIST OF REFERENCE SYMBOLS

1 Transparent body
2 Support surface
3 Peaks of the papillary ridges
4 Troughs of the papillary ridges
5 Surfaces of the troughs of the papillary ridges
8 Light source
9 Optical axis of the light bundle
10 Light bundle from the light source
11 Scattered light in the finger
12 Propagating light bundle
13, 14 Outermost light beams of the propagating light bundle
16 Optical axis of the imaging optical system
20 Diaphragm
21 Lenses
22 Light detector
23 Rectangular light-sensitive detector surface
25 Lateral surface of the transparent body
$\theta_{crit}$ Critical angle for total internal reflection at a glass/water interface
$\alpha$ Angle between the support surface and optical axis of the imaging optical system
$\beta$ Angle between the detector surface and optical axis of the imaging optical system
$n_1$ Optical refractive index of the transparent body
$n_2$ Optical refractive index of the medium between the support surface and finger surface
30 Mirror
31 Lateral surface
32 Integrated lens
40 Holding block
41 Frame
43 Lateral part of the holding block
44 Diaphragm
45 Deflecting mirror
50 Printed circuit board
51 Light-emitting diodes

The invention claimed is:

1. An apparatus for optically recording the papillary ridges on a finger surface,
   the apparatus having a transparent body with a support surface for a finger and with a lateral surface,
   as well as comprising a light source for illuminating the finger surface and an optical system for imaging the papillary ridges that lie on the support surface, and comprising a light detector,
   wherein the light source emits a light bundle that has a divergent angle that is smaller than the critical angle for total internal reflection at the support surface of the transparent body, and
   the light bundle leads through the transparent body and falls onto the support surface and irradiates the papillary ridges of the finger there, and
   the optical system for imaging the papillary ridges is adapted for propagating light bundle that emanates from the support surface and leads through the optical system in order to image the papillary ridges and falls onto a detector surface of the light detector and lies in an angular range that corresponds to the angular range in which light beams that are reflected at the support surface with water, lying thereupon, by total internal reflection,
   wherein the optical axis of the imaging optical system runs perpendicularly through the lateral surface of the transparent body and wherein the support surface of the transparent body arranged at a first angle to the optical axis of the imaging optical system, and the detector surface of the light detector is arranged at a second angle to the optical axis of the imaging optical system in accordance with the Scheimpflug principle.

2. The apparatus as claimed in claim 1, wherein the imaging optical system has a diaphragm.

3. The apparatus as claimed in claim 2, wherein the imaging optical system has a single lens or a plurality of lenses.

4. The apparatus as claimed in claim 3, wherein the imaging optical system has a mirror for the purpose of folding it.

5. The apparatus as claimed in claim 1 or 4, wherein the light source has at least one lens.

6. The apparatus as claimed in claim 1 or 4, wherein the light source has at least two light-emitting diodes that are arranged in a one- or two-dimensional array.

7. The apparatus as claimed in claim 1 or 4, wherein a diffuser is arranged between the light source and the transparent body.

8. The apparatus as claimed in claim 1 or 4, wherein the light detector has a two-dimensional CMOS camera or a CCD camera.

9. The apparatus as claimed in claim 1 or 4, wherein the transparent body consists of a high-index material with an optical reflective index of greater than 1.55.

10. The apparatus as claimed in claim 1 or 4, wherein the transparent body consists of a high-index material with an optical reflective index of greater than 1.55.

11. The apparatus as claimed in claim 10, wherein a focusing lens is integrated on a further lateral surface of the transparent body and/or in that a diaphragm is arranged outside the transparent body, there being arranged with particular preference outside the transparent body a deflecting mirror that directs the light focused by the integrated lens onto a printed circuit board on which the light detector and the light source are arranged.

12. The apparatus as claimed in claim 1 or 4, wherein the light source has at least two light-emitting diodes that are arranged in a one- or two-dimensional array and wherein said light-emitting diodes of the light source emit light in the red wavelength region from 650 to 780 nm or in the infrared wavelength region from 780 to 930 nm.

13. A method for operating the apparatus as claimed in claim 1, wherein the light source has at least two light-emitting diodes that are arranged in a one- or two-dimensional array, wherein the light-emitting diodes are respectively driven such that the light intensity they emit, is in accordance with the length of the light path from each light-emitting diode to the light detector and the light-sensitive surface of the light detector is thereby homogeneously illuminated.

14. The method as claimed in claim 13, wherein a first row of light-emitting diodes is driven such that the light intensity they emit is 60 to 80% of the light intensity that is emitted by a second row of light-emitting diodes.

15. The method as claimed in claim 13, wherein a middle row of light-emitting diodes is driven such that the light intensity they emit is approximately 30 to 70%, optionally approximately 50% of the light intensity that is emitted by two outer rows of light-emitting diodes.

* * * * *